United States Patent

Inaba

[11] Patent Number: 6,085,761
[45] Date of Patent: Jul. 11, 2000

[54] TOOTHPICK BRUSH

[75] Inventor: Osamu Inaba, Osaka Prefecture, Japan

[73] Assignee: Kabushiki Kaisha Koeisha, Osaka, Japan

[21] Appl. No.: 09/348,692

[22] Filed: Jul. 7, 1999

[30] Foreign Application Priority Data

Jul. 14, 1998 [JP] Japan ................................ 10-198523

[51] Int. Cl.[7] ............................. A61C 15/00; A61B 19/02
[52] U.S. Cl. ................................................ 132/329
[58] Field of Search ................................. 132/329, 321, 132/308, 309; 206/63.5; 433/216

[56] References Cited

U.S. PATENT DOCUMENTS

| | | | |
|---|---|---|---|
| 3,590,814 | 7/1971 | Bennett | 132/321 |
| 3,672,378 | 6/1972 | Silverman | 132/329 |
| 4,280,518 | 7/1981 | Gambaro | 132/329 |
| 4,617,694 | 10/1986 | Bori | 15/167 R |
| 4,911,187 | 3/1990 | Castillo | 132/329 |
| 5,507,646 | 4/1996 | Roth | 433/216 |
| 5,924,430 | 7/1999 | Baldauf | 132/321 |

FOREIGN PATENT DOCUMENTS 8201126  4/1982  WIPO ................................ 132/329

*Primary Examiner*—John J. Wilson
*Assistant Examiner*—Robyn Kieu Doan
*Attorney, Agent, or Firm*—Vedder Price Kaufman & Kammholz

[57] ABSTRACT

The invention relates to a toothpick brush comprising a brush body 11 provided with a point projecting portion 11 insertable in spaces between teeth, a gripping portion 12 formed so as to be easily held, and a connection part 13 for connecting the abovementioned two members; and a cleaning member 2 attached to the connection part 13. The cleaning member 2 is made of synthetic resin having rubber resiliency at a normal temperature, and a number of projecting brush elements 21 are formed on the outer circumferential surface of the cleaning member 2. According to the invention, stains and/or plaque between teeth can be securely removed by only one type of toothpick brush without impairing gums when using, and removal of stains between teeth and massaging of gums can be carried out at the same time.

1 Claim, 8 Drawing Sheets

TOOTHPICK BRUSH

BACKGROUND OF THE INVENTION

1. Field of the Invention

The present invention relates to a toothpick brush which removes stains and/or plaque accumulated in spaces between teeth and prevents decay of teeth and/or pyorrhoea alveolaris, etc., by massaging gums.

2. Description of the Related Arts

Conventionally, there are toothpicks made of wood or resin, and a between-teeth floss (thread toothpick) as those for removing stains accumulated between teeth. Further, a between-teeth brush having a brush wire made of resin attached at the tip end of its axis is available as a member for removing stains and/or plaque.

However, although the abovementioned toothpick is cheap and has an advantage in that stains between teeth can be favorably removed, it has a problem, by which gums, etc. are liable to be impaired, when inserting and using the toothpick between teeth. In addition, although the abovementioned between-teeth floss is able to very favorably remove stains by thread in very narrow spaces between teeth, there is another problem by which a thread is liable to be broken or cut off. In addition, although it is possible for the between-teeth brush to very favorably remove stains and/or plaque by moving the brush wire in and out of spaces between teeth, the between-teeth brush is expensive and is likely to impair gums, etc., by the brush wire attached to the tip end of its axis. Further, it was necessary to use several types of between-teeth brushes in compliance with the size of spaces between teeth. Still further, in order to keep teeth healthy, it is preferable that not only stains and/or plaque between teeth are removed, but also a massage of the gums is carried out. However, an object which can perform these at the same time has not been developed yet.

Therefore, it is an object of the invention to provide a toothpick brush which, by a single type of a toothpick brush, is able to securely remove stains and/or plaque between teeth without impairing gums when using, and to simultaneously massage the gums along with removing stains between teeth.

SUMMARY OF THE INVENTION

In order to achieve the abovementioned object, a toothpick brush according to the invention comprises a point projecting portion which is insertable into spaces between teeth; a gripping portion, a brush body provided with a connection part which connects the abovementioned two members, and a cleaning member attached to the abovementioned connection part, wherein the abovementioned cleaning member is made of synthetic resin having a rubber resiliency at a normal temperature, and has a number of projecting brush elements formed at the outer circumferential surface thereof.

With a toothpick brush according to the invention, by moving the cleaning member in and out of spaces between teeth by the point projection portion with the gripping portion of the brush body held, stains and/or plaque accumulated in spaces between teeth can be removed by the point projection portion and projecting brush elements of the cleaning member. At this time, the cleaning member is made of synthetic resin having a rubber resiliency at a normal temperature, and is formed of a number of projecting brush elements on the outer circumferential surface. Therefore, even though the size of spaces between teeth are different, it is possible to securely and safely remove stains and/or plaque in safety without impairing teeth and gums.

The cleaning member according to the invention is preferably formed to be of a rough trapezoid whose tip end is tapered. Many projecting brush elements are formed at three sides while a massaging portion for gums is formed on the bottom side, If so constructed, the loci connecting the tip ends of the projecting brush elements secured at the three sides of the cleaning member becomes triangular as the shape of spaces between teeth, whereby it becomes easy to insert the respective brush elements into the spaces between teeth, and an effect of removing stains and/or plaque between teeth can be improved by the respective brush elements. In addition, when taking the cleaning member in and out of spaces between teeth, the massaging portion secured on the bottom of the cleaning member is caused to be moved in and out while being brought into contact with the gums, thereby causing a massaging effect of the gums to be effectively obtained. Therefore, decay of teeth and/or pyorrhoea alveolaris, etc., can be prevented, and the massaging effect also contributes to the health of teeth.

It is preferable that the cleaning member is formed of elastomers whose hardness is 25 deg. through 95 deg. according to the JIS (Japanese Industrial Standards) A code. Synthetic resin harmless to human bodies, which has rubber resiliency at a normal temperature, such as synthetic rubber, polyisobuthylene, polyethylene, polyester, etc., may be used as the elastomers. In particular, Rabaron (SEBS), which is a brand name of Mitsubishi Chemical Co., Ltd., and Heptone (SEPS), which is a brand name of Kurare Co., Ltd., may be preferably used. By using such elastomers, it will become possible to securely and safely remove stains and/or plaque between teeth while giving a massaging effect to the gums, without impairing the teeth and gums.

Further, as a brush body, a material having shape retention and spring resiliency when being molded is preferable, a material which is a thermoplastic resin, for example, polypropyrene or a material obtained by blending polypropyrene with polyacetar, may be preferably used.

It is necessary that the cleaning member is attached to the brush body so that it is not separated therefrom. Therefore, the cleaning member may be fixed to the brush body by thermal fusion. However, it is preferable that a plurality of holes are formed at the connection part of the brush body and the cleaning member is linked with the brush body by using these holes. If so, the cleaning member and brush body can be integrally combined with each other via the holes. That is, since elastomers may be caused to flow into the holes of the brush body when integrally molding the cleaning member by causing elastomers to flow in the outer circumference of the brush body where the holes are formed, the brush body and cleaning member can be securely and tightly adhered to each other. Thereby, mass production of good quality toothpick brushes is enabled, and can be obtained at cheaper production costs in a simple manner in comparison with prior art between-teeth brushes. In addition, although it is preferable that the holes are through holes, which are through the brush body, the holes may be recess-like holes, which are not through holes.

DETAILED DESCRIPTION OF THE PREFERRED EMBODIMENT

A description is given of a preferred embodiment of the invention with reference to the accompanying drawings.

Figure 1:
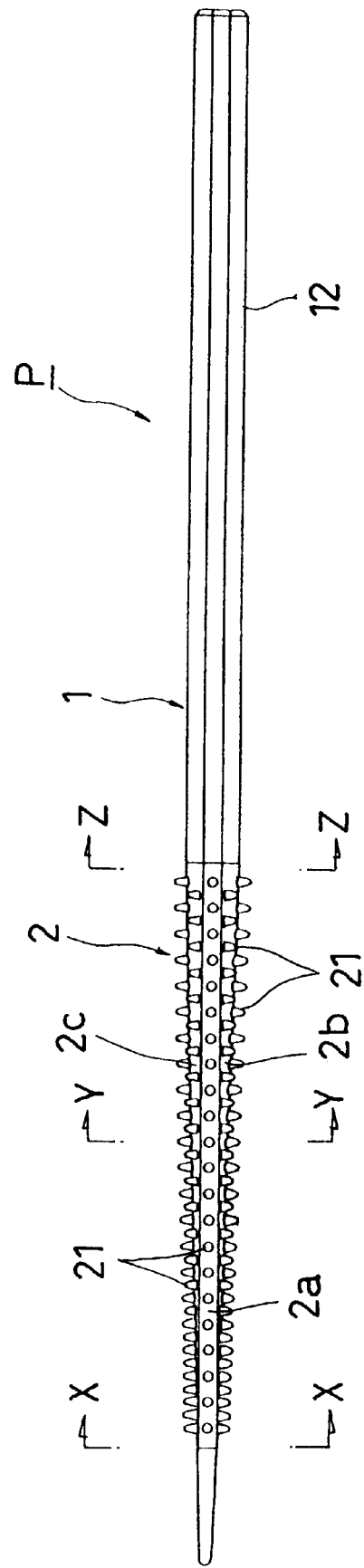
FIG. 1 is a plan view of a toothpick brush according to a preferred embodiment of the invention.
Figure 2:
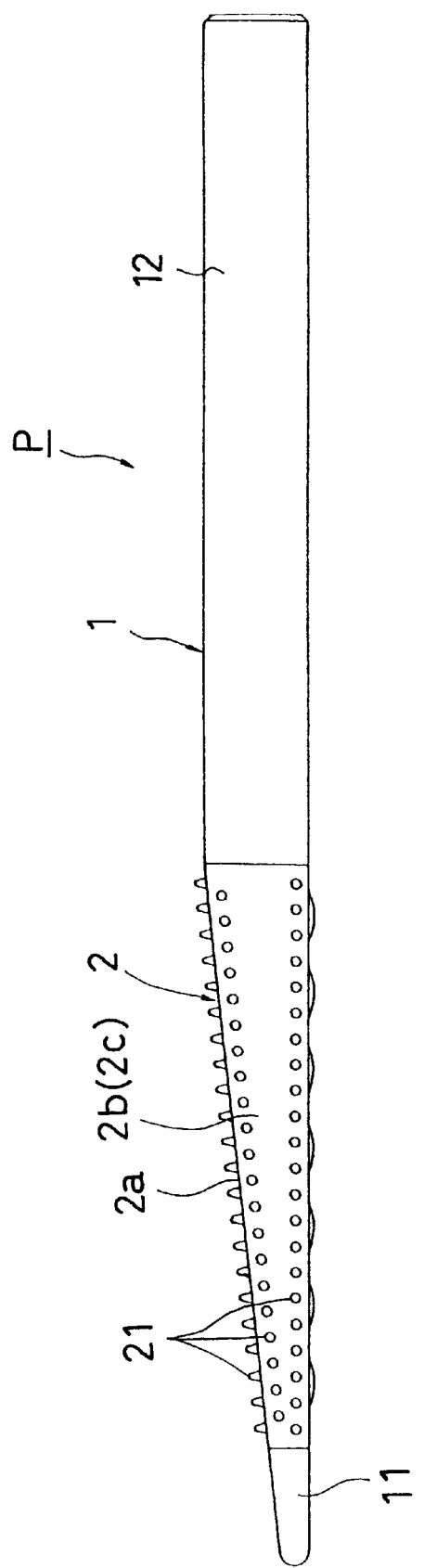
FIG. 2 is a front elevational view of the toothpick brush illustrated in FIG. 1.
Figure 3:
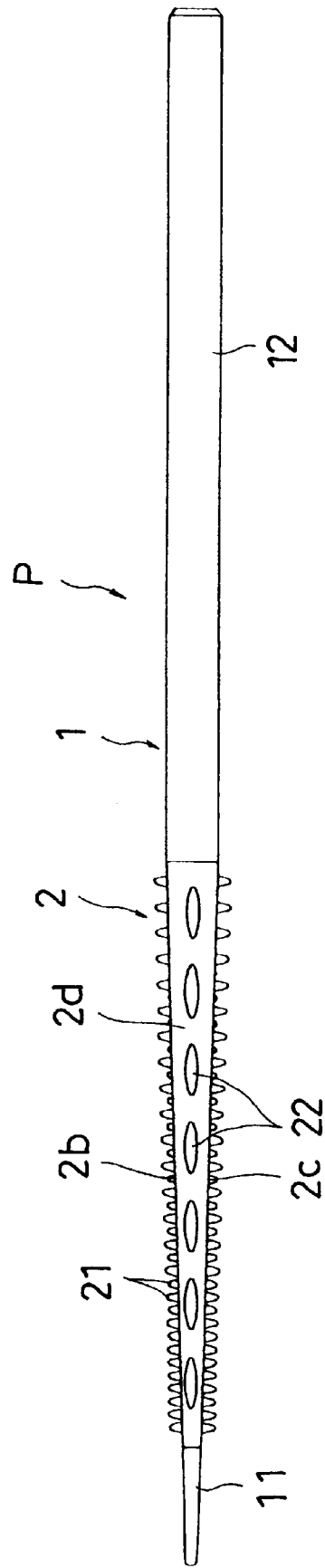
FIG. 3 is a bottom view of the toothpick brush illustrated in FIG. 1.
Figure 4:
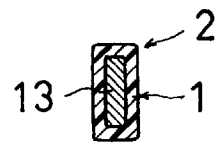
FIG. 4 is an enlarged cross-sectional view taken along the line X—X in FIG. 1.
Figure 5:
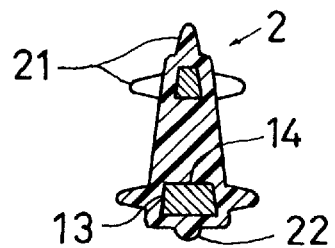
FIG. 5 is an enlarged cross-sectional view taken along the line Y—Y in FIG. 1.
Figure 6:
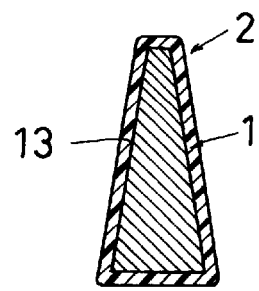
FIG. 6 is an enlarged cross-sectional view taken along the line Z—Z in FIG. 1.

A toothpick brush P illustrated in FIG. 1 through FIG. 3 is constructed by attaching a cleaning member 2 harmless to human bodies, which has rubber resiliency at normal temperature, to a plastic made brush body 1 having adequate hardness and resiliency.

As shown in the abovementioned plan view (FIG. 9) and front elevational view (FIG. 10), the brush body 1 is constructed of a point projecting portion 11 which is insertable into spaces between teeth, and a gripping portion 12 formed so as to be easily gripped, and a connection part 13 which connects the abovementioned two members. A number of holes 14 are formed at the connection part 13 of the brush body 1. The cleaning member 2 is integrally attached to the brush body 11 by utilizing the holes 14. In addition, elastomers such as synthetic rubber may be used as the cleaning member 2.

The point projecting portion 11 of the brush body 1 is entirely tapered so as to be flattened. In detail, for example, the length L1 is 4.5 mm, the lateral width L2 at the point end side is 0.5 mm, the lateral width L3 at the base end side is 0.7 mm, the height L4 at the point end side is 1.2 mm, and the height L5 at the base end side 1.5 mm. If the point projecting portion 11 is constructed as shown above, since the point projecting portion 11 can be inserted into any space between teeth, one type of a toothpick brush P can remove stains accumulated in the spaces between teeth. In addition, since the tip end of the point projecting portion 11 is made round, teeth and gums are never impaired when removing stains and/or plaque in spaces by inserting the point projecting portion 11 in the spaces between teeth.

Figure 7:
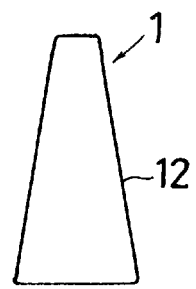
FIG. 7 is a right side view of the toothpick brush illustrated in FIG. 1.
Figure 8:
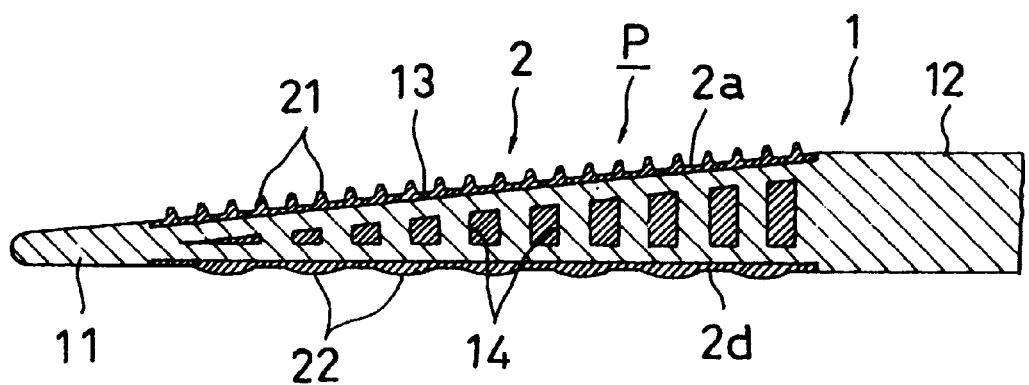
FIG. 8 is a longitudinally sectional view showing major parts of a toothpick brush.

As shown in the right side view (FIG. 7) of the brush body 1, the gripping portion 12 is formed so as to be like a trapezoid having the same dimension at its cross section in the entire lengthwise direction. Concretely, for example, the length L6 is 33.0 mm, the lateral width L7 at the upper side is 0.7 mm, the lateral width L8 at the lower end side is 2.0 mm, and the height L9 is 4.0 mm. With the construction, the gripping portion 12 can be easily gripped, whereby the maneuverabity of removing stains and/or plaque between teeth by the toothpick brush P is further improved.

Figure 9:
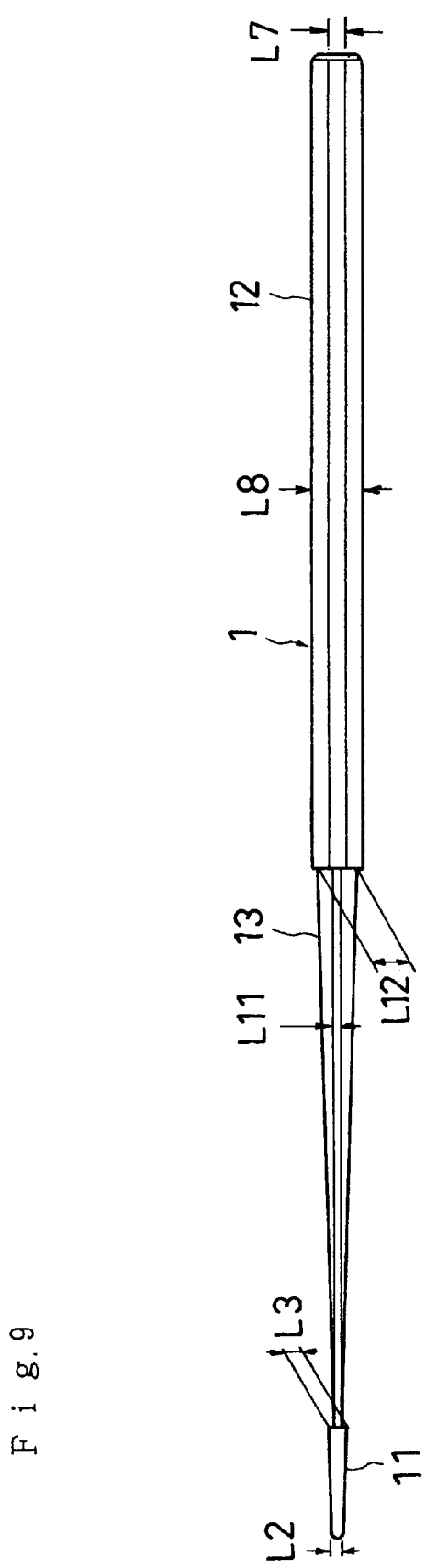
FIG. 9 is a plan view of a brush body.
Figure 10:
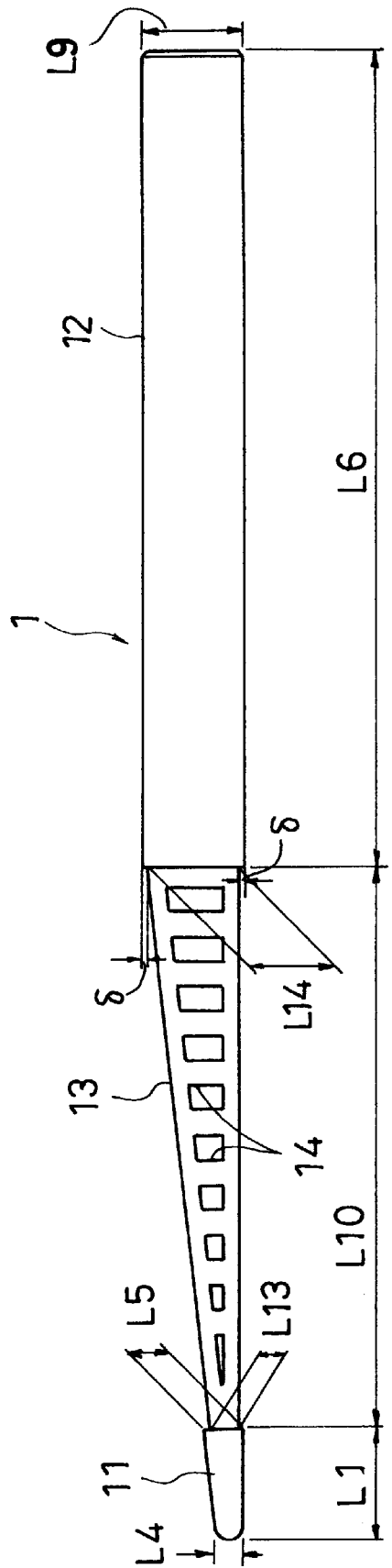
FIG. 10 is a front elevational view of the brush body.

Since the connection part 13 is formed so that its entire shape is tapered like a trapezoid, the connection part 13 is made continuous with a stage gap $\delta$ of 0.2 mm with respect to the point projecting portion 11 and gripping portion 12 (See FIG. 9 and FIG. 10). In detail, for example, the length L10 is 22.5 mm, the lateral width L11 at the upper and lower ends of the point end side and the lateral width L11 at the upper part of the other end are, respectively, 0.3 mm. Further, the lateral width L12 at the lower end side of the other end is 1.6 mm, the height L13 at the point end side is 1.1 mm, and the height L14 at the other end side is 3.6 mm. With the construction, L5–L13=2 $\delta$ and L9–L14=2 $\delta$ are established, whereby the point projecting portion 11, the connection part 13 and the gripping portion 12 are made continuous so as to form a stage gap $\delta$.

The cleaning member 2 which is tapered like a rough trapezoid is mounted at the connection part 13 shaped as shown above (See FIG. 4 through FIG. 6, and FIG. 8). By making the thickness of the body 0.2 mm which is equal to the abovementioned stage $\delta$, the outer circumferential surface of the body of cleaning member 2 can be made continuous to be flush with the outer circumferential surface of the point projecting portion 11 and gripping portion 12 (See FIG. 1 through FIG. 3, and FIG. 8).

As shown in FIG. 1 through FIG. 5, a number of projecting brush elements 21 which are each approximately 1 mm in height and diameter at the base end side are integrally provided on the cleaning member 2 so as to project at intervals of approximately 1 mm on both sides 2b and 2c, and top plane 2a. On the other hand, a massaging portions 22 for gums, which consist of elliptically shaped projection portions are integrally formed on the bottom 2d of the cleaning member 2.

The cleaning member 2 is mounted at the connection part 13 as described above. First, a plurality of holes 14 passing through both sides 2b and 2c are formed at the connection part 13 (See FIG. 8 and FIG. 10). Accordingly, when integrally molding the brush body 1 and cleaning member 2 by embedding the cleaning member 2 in the brush body 1 (that is, when forming the cleaning member 2 by causing elastomers to flow therein, using the brush body 1 as a core material), the elastomers are poured in the respective holes 14 secured on the brush body 1, and the brush body 1 and cleaning member 2 are firmly and tightly combined via the holes 14 (See FIG. 5 and FIG. 8). If the brush 1 and cleaning member 2 are thus constructed, a good quality toothpick brush P can be simply obtained at cheap production costs in comparison with prior arts between-teeth brushes. In addition, the holes 14 are not necessarily through holes, and the holes 14 may be recess-like holes by which the cleaning member 2 can be combined tightly.

Further, when mounting the cleaning member 2 at the connection part 13, a cleaning member 2 having projections which are engageable with the holes 14 is molded in advance without embedding, and the projection portions of the cleaning member 2 may be engaged with the holes 14, not depending on molding through embedding. In this case, the holes 14 are not necessarily through holes, and the holes 14 may be recess-like holes which are engageable with the projection portions of the cleaning member 2.

A description is given of actions when using the abovementioned toothpick brush P.

When removing stains and/or plaque accumulated between teeth, the gripping portion 12 of the brush body 1 is held by hand, and the cleaning member 2 is inserted between teeth from the point projecting portion 11 so as to be moved in and out of spaces between teeth, whereby stains and/or plaque accumulated between teeth are removed by the point projecting portion 11 and a number of projecting brush elements 21 formed on the cleaning member 2. At this time, since the cleaning member 2 is constructed so that the outer circumferential surface of the body (excluding the projecting brush elements) is tapered so as to continue flush toward the point projecting portion 11, the brush elements 21 can easily be inserted from the point projecting portion 11 without impairing teeth and gums even though the size of spaces between teeth is different. Therefore, using only one type of toothpick brush P, stains and/or plaque between the respective teeth can be securely and safely removed. In addition, since the entirety of the cleaning member 2 is made of elastomers and the top end of the point projecting portion 11 is made round, no fear of impairing teeth and gums is brought about, whereby safety is further increased.

Figure 11:
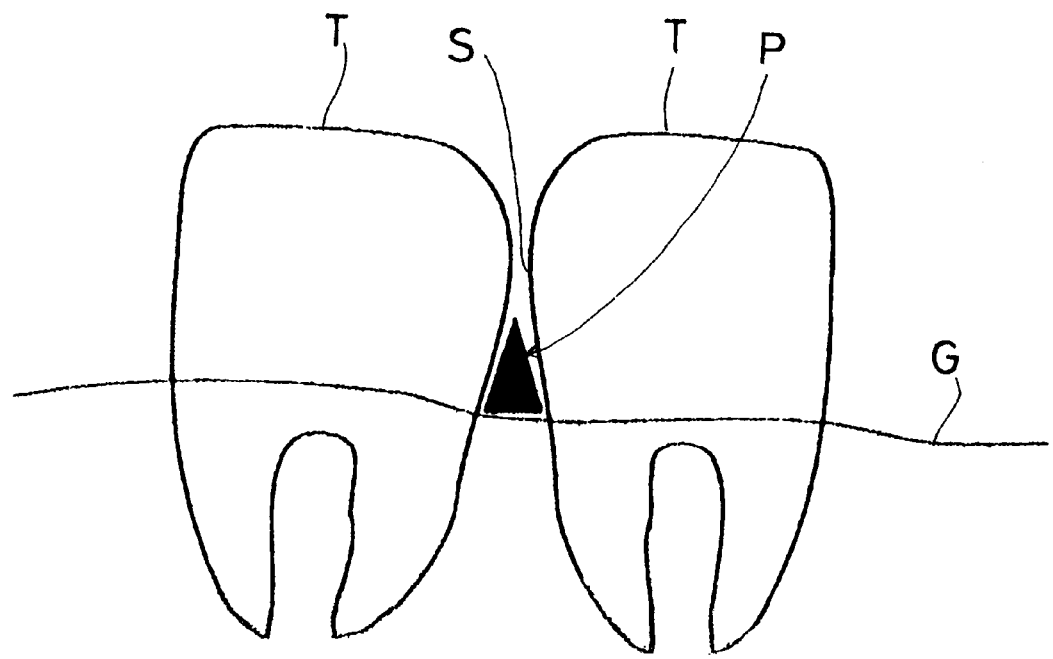
FIG. 11 is a rough sketch showing spaces between teeth.

Furthermore, the entire shape of the cleaning member 2 is trapezoidal, a number of projecting brush elements 21 are formed on both sides 2a, 2b and on the top surface 2c, and the loci depicting the top ends of the brush elements 21 is made triangular as in the space S between teeth T as shown in FIG. 11. Therefore, it becomes easy to insert the respective brush elements 21 into the space S, and an effect of removing stains and/or plaque between teeth by the respective brush elements 21 can be further increased. In addition, since the massaging portion 22 secured at the bottom surface 2d is moved in and out while being brought into contact with gums G when the cleaning member 2 is inserted in the spaces and caused to be moved in and out of the space S, a massaging effect of the gums G can be obtained, whereby decay of teeth and pyorrhoea alveolaris can be prevented to keep teeth healthy.

As described above, according to a toothpick brush of the invention, it is possible to securely remove stains and/or plaque between teeth with only one type of toothpick brush without impairing gums, etc., when using. In addition, removal of stains between teeth and massaging of gums can be obtained at the same time, and further, mass production of toothpick brushes can be facilitated.

While the invention has been described in connection with the preferred embodiment, it will be understood that modifications and variations thereof within the scope outlined above will be evident to those skilled in the art, and thus the invention is not limited to the preferred embodiment but is intended to encompass such modifications.

What is claimed is:

1. A toothpick brush comprising:

a brush body formed of synthetic resin having thermoplasticity, which has spring resiliency when being molded, having a point projecting portion insertable in spaces between teeth, a gripping portion, and a connection part for connecting said two portions; and a cleaning member attached to said connection part wherein a plurality of holes are formed at said connection part, and the cleaning member is combined to the brush body by said holes (wherein) and said cleaning member is made of synthetic resin having rubber resiliency at a normal temperature, and a number of projecting brush elements are formed on the outer circumferential surface thereof, constructed so that it is tapered and the entire shape thereof is roughly trapezoidal, and projecting brush elements are formed at three sides thereof while a massaging portion for gums is formed at the bottom thereof.

* * * * *